(12) United States Patent
Wolff et al.

(10) Patent No.: US 8,207,360 B2
(45) Date of Patent: Jun. 26, 2012

(54) PROPYLENE OXIDE PROCESS

(75) Inventors: Richard J. Wolff, Friendswood, TX (US); Kimberly A. Petry, Friendswood, TX (US); Blake S. Brown, Houston, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 12/657,896

(22) Filed: Jan. 29, 2010

(65) Prior Publication Data
US 2011/0190518 A1    Aug. 4, 2011

(51) Int. Cl.
C07D 301/12    (2006.01)
C07D 301/06    (2006.01)

(52) U.S. Cl. .......... 549/533; 549/531; 549/532

(58) Field of Classification Search .......... 549/531, 549/532, 533; 502/66
See application file for complete search history.

(56) References Cited

U.S. PATENT DOCUMENTS

| | | | |
|---|---|---|---|
| 3,578,568 A | 5/1971 | Washall | |
| 4,833,260 A | 5/1989 | Neri et al. | |
| 4,954,325 A | 9/1990 | Rubin et al. | |
| 5,006,206 A | 4/1991 | Shih et al. | |
| 5,129,996 A | 7/1992 | Shih | |
| 5,384,418 A | 1/1995 | Zajacek et al. | |
| 5,753,576 A | 5/1998 | Crocco et al. | |
| 5,973,171 A | 10/1999 | Cochran et al. | |
| 6,077,498 A | 6/2000 | Diaz Cabanas et al. | |
| 6,114,551 A | 9/2000 | Levin et al. | |
| 6,498,259 B1 * | 12/2002 | Grey et al. | 549/533 |
| 6,500,311 B1 | 12/2002 | Sawyer | |
| 6,500,969 B1 * | 12/2002 | Zhou et al. | 549/531 |
| 6,646,141 B2 | 11/2003 | Hofen et al. | |
| 6,881,852 B2 | 4/2005 | Sharma et al. | |
| 6,884,898 B1 | 4/2005 | Miller | |
| 7,084,284 B2 | 8/2006 | Miller | |
| 7,138,535 B1 | 11/2006 | Whitman et al. | |
| 7,238,817 B1 | 7/2007 | Han | |
| 7,279,145 B2 | 10/2007 | Balan | |
| 7,442,817 B1 | 10/2008 | Paparatto et al. | |
| 7,531,674 B2 * | 5/2009 | Ishino et al. | 549/531 |
| 2005/0211541 A1 | 9/2005 | Bassler et al. | |
| 2005/0240037 A1 | 10/2005 | Bassler et al. | |
| 2005/0250965 A1 | 11/2005 | Bassler et al. | |
| 2005/0252762 A1 | 11/2005 | Bassler et al. | |
| 2006/0006054 A1 | 1/2006 | Gobbel et al. | |
| 2006/0009648 A1 | 1/2006 | Gobbel et al. | |
| 2006/0205964 A1 | 9/2006 | Gobbel et al. | |
| 2009/0042718 A1 | 2/2009 | Kaminsky et al. | |

OTHER PUBLICATIONS

George N. Vayssilov, "Structural and Physicochemical Features of Titanium Silicalites," *Catal. Rev.-Sci. Eng.*, 1997, 39(3), pp. 209-251, Marcel Dekker, Inc.

Thomas Maschmeyer et al., "Heterogeneous catalysts obtained by grafting metallocene complexes onto mesoporous silica," *Nature*, 1995, vol. 378, pp. 159-162.

(Continued)

*Primary Examiner* — Taylor Victor Oh

(57) ABSTRACT

A process for producing propylene oxide from propylene is disclosed. The process comprises reacting propylene and an oxidant selected from the group consisting of hydrogen peroxide and oxygen in a slurry comprising a catalyst and a solvent having a boiling point of 110° C. or lower to produce a reaction mixture. The reaction mixture including the catalyst is distilled to produce a vapor stream comprising propylene, propylene oxide, and at least a portion of the solvent, and a slurry stream comprising the solvent and the catalyst. At least a portion of the slurry stream is recycled to the reaction step.

15 Claims, 2 Drawing Sheets

OTHER PUBLICATIONS

Peter T. Tanev et al., "Titanium-containing mesoporous molecular sieves for catalytic oxidation of aromatic compounds," *Nature*, 1994, vol. 368, pp. 321-323.

Avelino Corma et al. "Synthesis of Si and Ti-Si-MCM-48 mesoporous materials with controlled pore sizes in the absence of polar organic additives and alkali metal ions," *Chem. Commun.*, 1998, pp. 579-580.

Di Wei et al., "Catalytic behavior of vanadium substituted mesoporous molecular sieves," *Catalysis Today 51*, 1999, pp. 501-511, Elsevier.

* cited by examiner

PROPYLENE OXIDE PROCESS

FIELD OF THE INVENTION

The invention relates to a process for producing propylene oxide by reacting propylene and an oxidant in a slurry comprising a catalyst and a solvent.

BACKGROUND OF THE INVENTION

Propylene oxide is an important industrial chemical intermediate. Propylene oxide may be produced by oxidation of propylene with an oxidant such as hydrogen peroxide (U.S. Pat. Nos. 4,833,260, 5,753,576, and 7,442,817), or by direct oxidation of propylene with oxygen and hydrogen in a solvent in the presence of a catalyst (U.S. Pat. Nos. 7,138,535, 7,238,817, 7,279,145, and 5,973,171). These processes are often carried out in a slurry phase and the solid catalyst is separated from the liquid and/gas reactor effluent by filtration or centrifugation, which may occur in the reactor or outside the reactor, see, e.g., U.S. Pat. No. 7,084,284.

U.S. Pat. No. 6,884,898 teaches a continuous propylene oxide production process comprising reacting propylene with molecular oxygen and hydrogen in the presence of a solvent having a boiling point of at least 130° C. and a solid noble metal on titanium silicalite catalyst. Methanol and water may be present in the reaction. The process includes flashing lower boiling components comprising propylene oxide as vapor from a reaction liquid stream and recycling a slurry of the solvent and the catalyst from the flashing step to the reaction step.

SUMMARY OF THE INVENTION

The invention is a process for making propylene oxide from propylene. The process comprises reacting propylene and an oxidant selected from the group consisting of hydrogen peroxide and oxygen in a slurry comprising a catalyst and a solvent having a boiling point of 110° C. or lower to produce a reaction mixture comprising propylene, propylene oxide, the solvent and the catalyst (oxidation step). The reaction mixture is distilled to produce a vapor stream comprising propylene, propylene oxide, and at least a portion of the solvent, and a slurry stream comprising the solvent and the catalyst. At least a portion of the slurry stream is recycled to the oxidation step.

DETAILED DESCRIPTION OF THE INVENTION

Figure 1:
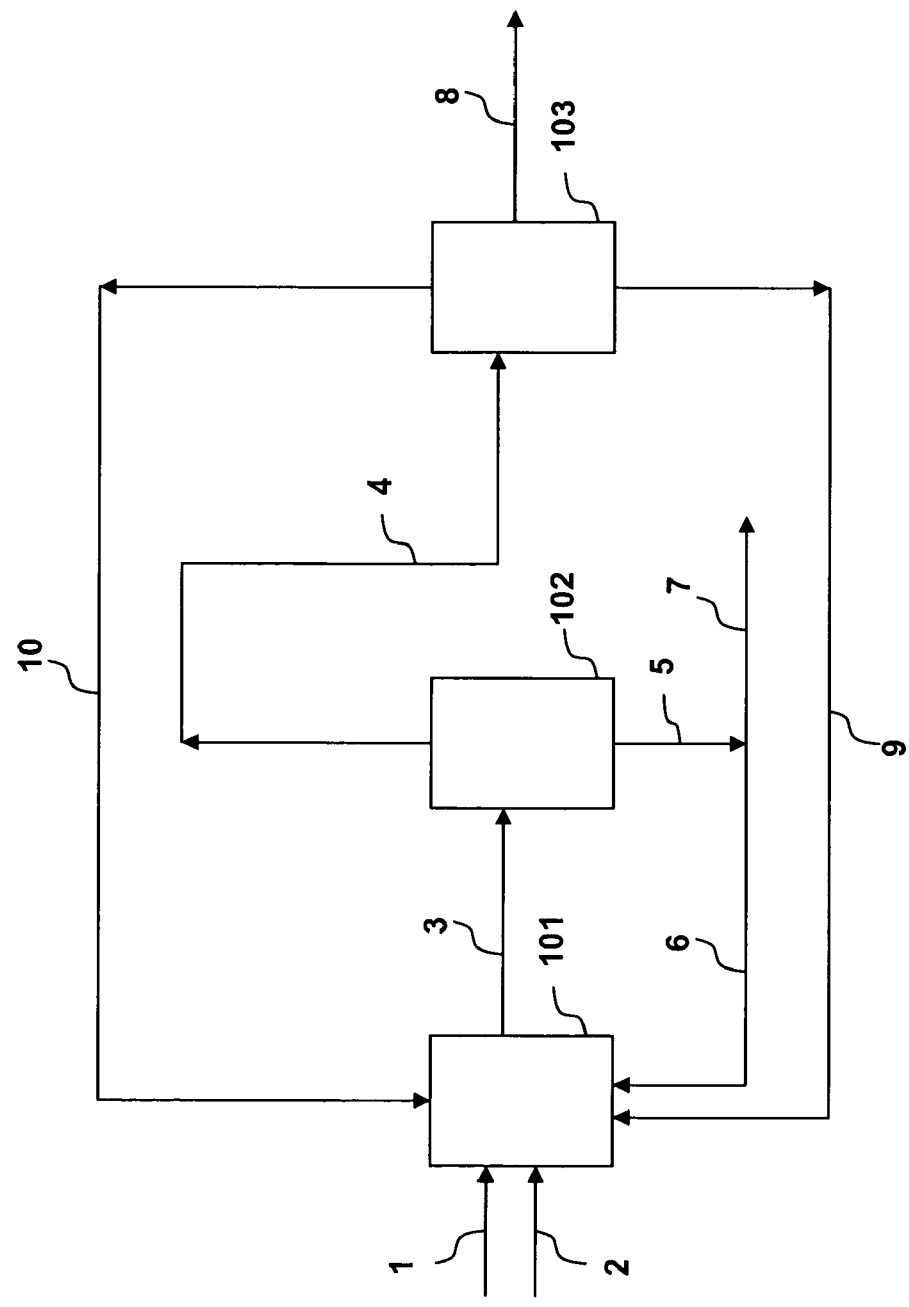
FIG. 1 shows a process for producing propylene oxide employing a flash separator.

The process comprises reacting propylene and an oxidant selected from the group consisting of hydrogen peroxide and oxygen. The process uses propylene.

The process may use hydrogen peroxide as an oxidant, preferably an aqueous solution. The hydrogen peroxide concentration is generally from 1 to 50 wt %, preferably of from 5 to 30 wt %. The aqueous hydrogen peroxide solution may contain other organic components. A hydrogen peroxide solution prepared from a reaction between a secondary alcohol (e.g., isopropanol or methyl benzyl alcohol) with oxygen may be used. For example, U.S. Pat. No. 5,384,418 describes a process involving oxidation of an aliphatic secondary alcohol by oxygen to produce a hydrogen peroxide solution, which is used to oxidize an olefin to produce an epoxide.

The process may use oxygen as an oxidant. When oxygen is used as an oxidant, hydrogen is preferably used as well. The molar ratio of hydrogen to oxygen can usually be varied in the range of 1:100 to 10:1 and is especially favorable at 1:5 to 2:1. The molar ratio of oxygen to propylene is usually 1:1 to 1:20, and preferably 1:1.5 to 1:10.

The process may use an inert gas. Suitable inert gases include nitrogen, helium, argon, and carbon dioxide. Saturated hydrocarbons with 1 to 4 carbon atoms, e.g., methane, ethane, propane, and n-butane, may be used. Mixtures of the inert gases can be used. The molar ratio of propylene to inert gas is usually in the range of 100:1 to 1:20 and especially 20:1 to 1:20.

A suitable catalyst for the process comprises a transition metal zeolite. Zeolites generally contain one or more of Si, Ge, Al, B, P, or the like, in addition to oxygen. A transition metal zeolite (e.g., titanium zeolite, vanadium zeolite) is a crystalline material having a porous molecular sieve structure and containing a transition metal. A transition metal is a Group 3-12 element. The first row of these includes elements from Sc to Zn. Preferred transition metals are Ti, V, Mn, Fe, Co, Cr, Zr, Nb, Mo, and W. Particularly preferred are Ti, V, Mo, and W. Most preferred is Ti. The type of transition metal zeolite employed depends upon a number of factors, including the size and shape of the olefin to be epoxidized. For example, it is especially advantageous to use titanium silicalite-1 (TS-1, a titanium silicalite having an MFI topology analogous to that of the ZSM-5 aluminosilicate) for the epoxidation of propylene.

Suitable titanium zeolites include titanium silicates (titanosilicates). Preferably, they contain no element other than titanium, silicon, and oxygen in the lattice framework. Small amounts of impurities, e.g., boron, iron, aluminum, phosphorous, copper, and mixtures thereof, may be present in the lattice. The amount of impurities is preferably less than 0.5 weight percent (wt %), more preferably less than 0.1 wt %. Preferred titanium silicates will generally have a composition corresponding to the following empirical formula: $xTiO_2 \cdot (1-x)SiO_2$, where x is between 0.0001 and 0.5. More preferably, the value of x is from 0.01 to 0.125. The molar ratio of Si to Ti in the lattice framework of the zeolite is advantageously from 9.5:1 to 99:1 (most preferably from 9.5:1 to 60:1). Particularly preferred titanium zeolites include the class of molecular sieves commonly known as titanium silicalites (see *Catal. Rev.-Sci. Eng.* 39(3) (1997) 209). Examples of these include TS-1 and TS-2 (having an MEL topology analogous to that of the ZSM-11 aluminosilicate). Titanium zeolites having framework structures isomorphous to zeolite beta, mordenite, ZSM-12, MCM-22, MCM-41, and MCM-48 are also suitable for use. Examples of MCM-22, MCM-41, and MCM-48 zeolites are described in U.S. Pat. Nos. 4,954,325, 6,077,498, and 6,114,551; Maschmeyer, T., et al, *Nature* 378(9) (1995) 159; Taney, P. T., et al., *Nature* 368 (1994) 321; Corma, A., *J. Chem. Soc., Chem. Commun.* (1998) 579; Wei D., et al., *Catal. Today* 51 (1999) 501).

If oxygen is used as an oxidant, the catalyst also comprises a noble metal in addition to the transition metal zeolite. Suitable noble metals include, e.g., gold, silver, platinum, palladium, iridium, ruthenium, rhenium, rhodium, osmium, and mixtures thereof. Preferred noble metals are Pd, Pt, Au, Re, Ag, and mixtures thereof. A catalyst comprising palladium is particularly preferred. Typically, the amount of noble metal present in the catalyst will be in the range of from 0.01 to 20 wt %, preferably from 0.1 to 5 wt %.

The noble metal and the transition metal zeolite may be on a single solid particle or on separate ones. For example, the noble metal may be supported on the transition metal zeolite. Alternatively, the catalyst may comprise a mixture of a transition metal zeolite and a noble metal supported on a carrier. Suitable carriers for the supported noble metal include carbons, titanias, zirconias, niobias, silicas, aluminas, silica-aluminas, titania-silicas, ion-exchange resins, and the like, and mixtures thereof.

The manner in which the noble metal is incorporated into the catalyst is not critical. For example, the noble metal may be supported on the transition metal zeolite or other carriers by impregnation, ion exchange, adsorption, precipitation, or the like.

The weight ratio of the transition metal zeolite to the noble metal is not particularly critical. However, a transition metal zeolite to noble metal ratio of 10 to 10000 (grams of transition metal zeolite per gram of noble metal) is preferred.

The catalyst particles generally have a mean mass diameter of from 0.1 to 500 μm, preferably from 1 to 100 μm. The amount of the catalyst in a reactor is typically 1 wt % to 20 wt % of the reactor content, preferably 2 to 10 wt %.

The reactor content is typically well mixed. Any suitable method for mixing a gas and a slurry may be used. For example, a mechanical agitator can be used.

The reaction is conducted in slurry comprising a catalyst and a solvent having a boiling point of 110° C. or lower. Suitable solvents include, for example, oxygen-containing hydrocarbons such as alcohols, nitriles such as acetonitrile, and water. Suitable oxygenated solvents include alcohols, ketones, water, and the like, and mixtures thereof. Preferred oxygenated solvents include water, methanol, ethanol, isopropanol, tert-butanol, and mixtures thereof. Particularly preferred oxygenated solvents are selected from the group consisting of water, methanol, and mixtures thereof. If oxygen is used as the oxidant, a particularly preferred solvent is tert-butanol or a mixture of tert-butanol and water.

The process may use a buffer. The buffer is employed in the reaction to inhibit the formation of propylene glycols or glycol ethers during the epoxidation, and it can improve the reaction rate and selectivities. The buffer is typically added to the solvent to form a buffer solution, or the solvent and the buffer are added separately. Useful buffers include any suitable salts of oxyacids, the nature and proportions of which in the mixture are such that the pH of their solutions preferably ranges from 3 to 12, more preferably from 4 to 10, and most preferably from 5 to 9. Suitable salts of oxyacids contain an anion and a cation. The anion may include phosphate, carbonate, bicarbonate, sulfate, carboxylates (e.g., acetate), borate, hydroxide, silicate, aluminosilicate, or the like. The cation may include ammonium, alkylammonium (e.g., tetraalkylammoniums, pyridiniums), alkylphosphonium, alkali metal, and alkaline earth metal ions, or the like. Examples include $NH_4$, $NBu_4$, $NMe_4$, Li, Na, K, Cs, Mg, and Ca cations. The preferred buffer comprises an anion selected from the group consisting of phosphate, carbonate, bicarbonate, sulfate, hydroxide, and acetate; and a cation selected from the group consisting of ammonium, alkylammonium, alkylphosphonium, alkali metal, and alkaline earth metal ions. Buffers may preferably contain a combination of more than one suitable salt. Typically, the concentration of the buffer in the solvent is from 0.0001 M to 1 M, preferably from 0.0005 M to 0.3 M. The ammonium phosphates buffer is particularly preferred.

The reaction step is typically performed at a temperature in the range of from 30 to 100° C., preferably in the range of from 50 to 70° C., and at a pressure in the range of from 100 to 800 psig, preferably in the range of from 150 to 400 psig. A cooling coil is preferably used to remove the heat of the reaction.

The process comprises separating the reaction mixture including the catalyst into a vapor stream comprising propylene oxide, propylene, and at least a portion of the solvent, and a slurry stream comprising the solvent and the catalyst. If oxygen and hydrogen are used in the reaction step, the vapor stream may additionally comprise hydrogen and oxygen.

The separation of the reaction mixture is performed in a distillation column with many suitable tray designs, for example, bubble cap trays, valve trays, and sieve trays. A bubble cap tray has riser or chimney fitted over each hole, and a cap that covers the riser. The cap is mounted so that there is a space between riser and cap to allow the passage of vapor. Vapor rises through the chimney and is directed downward by the cap, discharging through slots in the cap, and bubbling through the slurry on the tray. In valve trays, perforations are covered by liftable caps. Vapor flows lifts the caps, thus self creating a flow area for the passage of vapor. The lifting cap directs the vapor to flow horizontally into the slurry, thus providing vapor/slurry mixing. Sieve trays are metal plates with holes in them. Vapor passes straight upward through the slurry on the plate.

A single stage distillation, also called flash evaporation or flash separation, may be used. Generally flash evaporation occurs in a vessel (flash separator or flash drum) that is at a lower pressure than that of the reaction mixture prior it enters the vessel so vaporization occurs under a reduced pressure. The pressure in the flash separator is typically controlled at 14 to 300 psig, preferably 14 to 100 psig. A heating device may be installed within the flash separator to facilitate the evaporation of lighter components. Alternatively, the reaction mixture may be heated to a higher temperature by an external heating device before it enters the flash separator. The temperature of the flash separator is typically at 60 to 200° C., preferably at 70 to 150° C.

A scrubber may be used together with the flash separator. The vapor from the top of the flash separator may be contacted with a solvent in the scrubber. Any conventional distillation column may be used as a scrubber. A fresh solvent or a recycled solvent may be used as a scrubbing liquid. The scrubber is generally operated at a temperature of 65 to 115° C.

The reaction mixture is separated into a vapor stream and a slurry stream. The vapor stream comprises propylene, propylene oxide, and the solvent. The slurry stream comprises the catalyst, the solvent, and other components. Preferably greater than 80%, more preferably greater than 90% of propylene oxide from the reaction mixture is distributed in the vapor stream.

A stripping agent may be added to the distillation to vaporize lighter components such as propylene oxide and propylene from the slurry. Conveniently propylene is used as the stripping agent. Preferably the stripping agent is fed to the bottom of a distillation column (e.g., a flash separator) to maximize its contact with the slurry.

The vapor stream, which contains mostly propylene, propylene oxide and the solvent, is further processed to produce propylene oxide. Many techniques for separating propylene oxide from the vapor stream may be used. Typically an extractive distillation method is used. See, e.g., U.S. Pat. Nos. 3,578,568, 5,006,206, and 5,129,996. Other propylene oxide separation or purification techniques can be found in U.S. Pat. Nos. 6,500,311, 6,646,141, 6,881,852; U.S. Pat. Appl. Pub. Nos. 2005/0252762, 2005/0250965, 2005/0211541, 2005/0240037, 2006/0009648, 2006/0205964, and 2006/0006054.

Propylene and other gases separated from the vapor stream are preferably recycled to the reaction step.

At least a portion of the slurry stream from the distillation is recycled to the reaction step. The rest of the slurry stream may be distilled to separate the catalyst from the solvent. The separated catalyst may be activated before it is reused in the reaction step. The solvent recovered from the slurry may be recycled to the process.

Example 1

The following is one proposed method of practicing the process of the invention.

A process for producing propylene oxide from propylene, oxygen, and hydrogen is shown in FIG. 1. A catalyst containing titanium silicate-1 and Pd—Au supported on titania as described in Example 2 of the U.S. Pat. Appl. Pub. No. 2009/0042718 may be used. Fresh propylene, hydrogen, nitrogen, methanol, water, and an ammonium phosphate buffer solution enter reactor 101 via line 1. Fresh oxygen enters the reactor 101 via line 2. A recycled slurry stream containing catalyst enters reactor 101 via line 6. A recycled solvent stream containing methanol and water enters reactor 101 via line 9. The reaction is operated at 60° C. and under pressure of 300 psig.

The reaction mixture containing 1.2 wt % propylene, 5.3 wt % propane, 4.6 wt % propylene oxide, less than 1 wt % hydrogen, less than 1 wt % oxygen, 56.2 wt % methanol, 20.3 wt % water, 0.06 wt % ammonium phosphate, and 7.8 wt % catalyst is passed to flash separator 102 having an diameter of about 18 ft at a flow rate of about 1,585,000 lb/h. Other reaction by products such as propylene glycol, propylene glycol methyl ethers, and methyl formate are also present in the reaction mixture. The flash separator is operated at 15 psig and maintained at 76° C. The slurry stream from flash separator 102 comprising 0.66 wt % propylene oxide, 39.3 wt % methanol, 31.2 wt % water, 0.16 wt % ammonium phosphate, and 21.2 wt % catalyst exits flash separator 102 via line 5 and is recycled to the reactor via line 6. A portion of the slurry stream may be segregated via line 7, which may be filtered to isolate the catalyst for regeneration or disposal. The vapor stream comprising 6.9 wt % propylene oxide, 8.4 wt % propane, less than 1 wt % oxygen, less than 1 wt % hydrogen, 66.2 wt % methanol, 13.9 wt % water, and others is passed via line 4 to propylene oxide purification section 103 wherein propylene oxide is separated via line 8. A mixture containing methanol and water is recovered from section 103 and recycled to reactor 101 via line 9. A gas mixture separated from the vapor stream including propylene, oxygen, and hydrogen is recycled to reactor 101 via line 10.

Example 2

Figure 2:
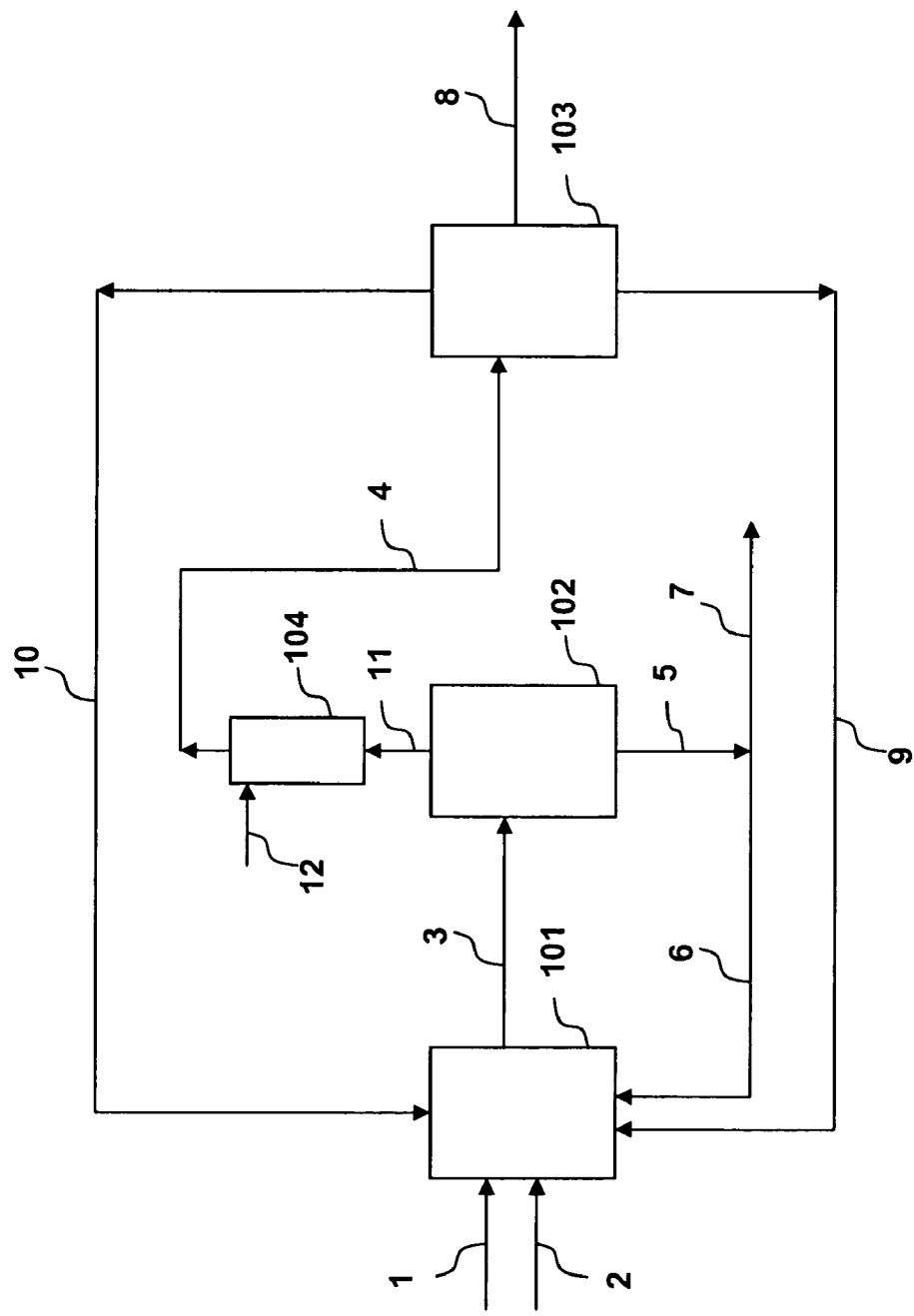
FIG. 2 shows a process for producing propylene oxide employing a flash separator and a scrubber.

FIG. 2 shows another proposed method of practicing the invention.

The reaction is operated at 60° C. and under pressure of 300 psig. The reaction mixture containing 1.2 wt % propylene, 5.3 wt % propane, 4.6 wt % propylene oxide, less than 1 wt % hydrogen, less than 1 wt % oxygen, 56.2 wt % methanol, 20.3 wt % water, 0.06 wt % ammonium phosphate, 7.8 wt % catalyst, and other components is passed to flash separator 102 with an diameter of about 18 ft at a flow rate of about 1,585,000 lb/h. The flash separator is operated at 15 psig and maintained at 76° C. The vapor from the flash separator enters scrubber 104 via line 11. The scrubber has a diameter of 16 ft and contains 10 conventional trays. A purified solvent stream containing methanol and water in a weight ratio of 88:12 recovered from purification section 103 is fed to the top portion of the scrubber at a rate of 70,000 lb/h via line 12. The scrubber 104 is operated at a pressure of 15 psig. The scrubbed vapor stream exit the top of the scrubber at a rate of 1,114,000 lb/h. It contains 6.2 wt % propylene oxide, 7.6 wt % propane, less than 1 wt % oxygen, less than 1 wt % hydrogen, 67.5 wt % methanol, 14.6 wt % water, and others. It is passed via line 4 to purification section 103 wherein propylene oxide is separated via line 8. A recovered solvent containing methanol and water is recovered from section 103 and partly recycled to reactor 101 via line 9. A portion of the recovered solvent is used in scrubber 104. A gas mixture separated from the vapor stream including propylene, oxygen, and hydrogen is recycled to reactor 101 via line 10.

The slurry stream exits the flash separator 102 at a rate of 541,000 lb/h. It contains 0.7 wt % propylene oxide. 36.4 wt % methanol, 31.7 wt % water, 0.18 wt % ammonium phosphate, and 23.0 wt % catalyst, and is recycled to the reactor via line 6.

We claim:

1. A process for producing propylene oxide comprising (a) reacting propylene and an oxidant selected from the group consisting of hydrogen peroxide and oxygen, in the presence of a solvent having a boiling point of 110 degree C or lower and a catalyst comprising a transition metal zeolite to form a reaction mixture comprising propylene oxide, propylene, the solvent, and the catalyst; (b) distilling the reaction mixture into a vapor stream comprising propylene oxide, propylene, and at least a portion of the solvent, and a slurry stream comprising the solvent and the catalyst; (c) recycling a portion of the slurry stream to step (a); (d) distilling the remaining portion of the slurry stream into the catalyst and the solvent (e) activating the distilled catalyst; (f) recycling the activated distilled catalyst to step (a); (g) recycling the distilled solvent to step (a).

2. The process of claim 1 wherein the oxidant is hydrogen peroxide.

3. The process of claim 1 wherein the solvent is methanol, water, or a mixture of methanol and water.

4. The process of claim 1 wherein the oxidant is oxygen.

5. The process of claim 4 wherein step (a) is performed in the presence of hydrogen.

6. The process of claim 5 wherein the catalyst further comprises a noble metal.

7. The process of claim 4 wherein the solvent is tert-butanol or a mixture of tert-butanol and water.

8. The process of claim 1 wherein the vapor stream has greater than 80% of the propylene oxide formed in step (a).

9. The process of claim 1 wherein the vapor stream has greater than 90% of the propylene oxide formed in step (a).

10. The process of claim 1 wherein step (b) is performed in a flash separator.

11. The process of claim 10 wherein a scrubber is used in step (b).

12. The process of claim 10 wherein the flash separator has an internal heater.

13. The process of claim 10 wherein the reaction mixture is heated before it enters the flash separator.

14. The process of claim 1 wherein a stripping agent is used in step (b).

15. The process of claim 14 wherein the stripping agent comprises propylene.

* * * * *